… …

United States Patent [19]

Kulisz et al.

[11] Patent Number: 5,618,257

[45] Date of Patent: Apr. 8, 1997

[54] BLADDER CONTROL INSERTION APPARATUS AND METHOD

[75] Inventors: Andre A. Kulisz; Valery Migachyov, both of San Antonio, Tex.

[73] Assignee: HK Medical Technologies Incorporated, San Antonio, Tex.

[21] Appl. No.: 515,564

[22] Filed: Aug. 16, 1995

[51] Int. Cl.$^6$ ...................................................... A61F 2/00
[52] U.S. Cl. ................................................................ 600/29
[58] Field of Search ........................ 600/29, 30; 128/885; 604/97–99, 51

[56] References Cited

U.S. PATENT DOCUMENTS

| | | | |
|---|---|---|---|
| 3,731,670 | 5/1973 | Loe | 128/1 R |
| 3,812,841 | 5/1974 | Isaacson | 128/1 R |
| 4,553,533 | 11/1985 | Leighton | 128/1 R |
| 4,679,546 | 7/1987 | van Waalwijk van Doorn et al. | 128/1 R |
| 4,934,999 | 6/1990 | Bader | 600/29 |
| 4,955,858 | 9/1990 | Drews | 604/8 |
| 4,968,294 | 11/1990 | Salama | 600/30 |
| 4,969,474 | 11/1990 | Schwarz | 128/885 |
| 5,007,894 | 4/1991 | Enhorning | 600/29 |
| 5,007,898 | 4/1991 | Rosenbluth et al. | 604/54 |
| 5,012,822 | 5/1991 | Schwarz | 128/885 |
| 5,041,092 | 8/1991 | Barwick | 604/104 |
| 5,078,676 | 1/1992 | Bailly | 600/31 |
| 5,088,980 | 2/1992 | Leighton | 600/30 |
| 5,090,424 | 2/1992 | Simon et al. | 128/885 |
| 5,097,848 | 3/1992 | Schwarz | 128/885 |
| 5,112,306 | 5/1992 | Burton et al. | 604/101 |
| 5,114,398 | 5/1992 | Trick et al. | 600/29 |
| 5,123,428 | 6/1992 | Schwarz | 128/885 |
| 5,140,999 | 8/1992 | Ardito | 128/885 |

FOREIGN PATENT DOCUMENTS

| | | | |
|---|---|---|---|
| WO96/18431 | 6/1996 | WIPO | |

*Primary Examiner*—Lee S. Cohen
*Assistant Examiner*—Herman J. Robinson
*Attorney, Agent, or Firm*—Nawrocki, Rooney & Sivertson

[57] ABSTRACT

Insertion apparatus for a female bladder control device including an outer tube for insertion into the urethra of a patient, the outer tube having an inner lumen and a retention collar for limiting the depth of insertion of the outer tube. A dilator probe with a tapered end, the probe sized for slidable movement into the outer tube and the probe having stop means engagable by the first tube to limit the depth of insertion of the probe tapered end into the urethra. An applicator tube sized for slidable positioning within the outer tube and having an inner lumen for removably carrying a bladder control device for placement within the lumen. Also provided is an insertion device for moving the bladder control device into the second tube. The preferred embodiment described in this disclosure includes a spring-type retaining device mounted on one end of the placed bladder control device and an additional retainer on the other end for retaining the placed bladder control device within the urethra.

10 Claims, 12 Drawing Sheets

BLADDER CONTROL INSERTION APPARATUS AND METHOD

CROSS REFERENCE TO CO-PENDING APPLICATIONS

The present invention is related to the following U.S. Patent Applications which are assigned to the assignee of the present invention and incorporated herein by reference:

| | | |
|---|---|---|
| 07/969,928 | SELF-CONTAINED INTRAURETHRAL BLADDER CONTROL DEVICE | Abandoned |
| 08/173,636 | NONSURGICAL INTRAURETHRAL BLADDER CONTROL DEVICE | Abandoned |
| 08/298,033 | NONSURGICAL INTRAURETHRAL BLADDER CONTROL DEVICE. | Abandoned |

BACKGROUND OF THE INVENTION

1. Field of the Invention

The present invention relates generally to medical devices; more particularly to bladder control devices; and still more particularly to insertion apparatus for placement of bladder control apparatus within the urethra of a patient.

2. Description of the Prior Art

The value and advantages of bladder control apparatus, often referred to as artificial sphincters, is well-known to those of skill in the medical art. As can be seen in the prior art, it is desirable to place certain bladder control devices within the urethra of a patient for direct control of the flow of fluid form the bladder through the urethra and thence from the patient. The prior art has recognized various devices for such implantation of bladder control apparatus. Certain of these prior art devices have the disadvantage of being somewhat difficult or clumsy for the medical personnel to manipulate during insertion, and others carry the disadvantage of potentially damaging the urethra or the bladder, for example, if an insertion device is placed too far into the bladder from the urethra and damages the bladder wall.

It is to overcome these potential disadvantages and to provide a sure and simple insertion device that the present invention has been made.

SUMMARY OF THE INVENTION

The present invention overcomes the disadvantages of the prior art by providing a method and apparatus for atraumatically inserting and removing a bladder control apparatus.

In the preferred mode of practicing the present invention, the insertion apparatus consists of an outer tube having a retention collar, a solid urethral dilation probe, a device handling tube, and a device insertion rod, in addition to the bladder control device. The outer tube has a length greater than that of the urethra and a lumen of sufficient size to slideably accommodate the solid urethral dilation probe. Using suitable topical lubricants, antiseptics, and pain control, the dilation probe is inserted through the lumen of the outer tube, and the assembly is advanced through the urethra, until the neck of the bladder is located via manual sensation. The dilation probe is removed leaving the outer tube extending the entire length of the urethra and about 1 cm. into the bladder. The distal end of the outer tube is stabilized by sliding the retention collar proximally until it rests against the meatus, where it is removably locked in place by a retention screw.

The device handling tube has an outside diameter sufficiently small to position slideably within the distal end of the outer tube and has an inside diameter sufficiently large to slideably accommodate the bladder control device. The bladder control device is loaded into the device handling tube to restrain the proximal retaining elements of the bladder control device against the inner walls of the device handling tube. The insertion rod is removably attached to the distal end of the bladder control device. The proximal end of the device handling tube is inserted into the distal end of the outer tube and the bladder control device is advanced proximally into the outer tube. The device handling tube is removed distally from the insertion rod.

The insertion rod is advanced proximally until the bladder control device traverses the length of the outer tube permitting the retaining means to expand within the bladder. The outer tube and its retention collar are removed from the patient leaving the bladder control device and insertion rod in place. The insertion rod is pulled distally until the distal end of the bladder control device is visually positioned at the distal end of the urethra. This assumes that the bladder control device is of a proper length which may necessitate the use of an extension. The insertion rod is disconnected from the bladder control device and the distal retaining ring is attached. Removal of the bladder control device is accomplished using the reverse of the above explained procedure.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENT

Figure 1:
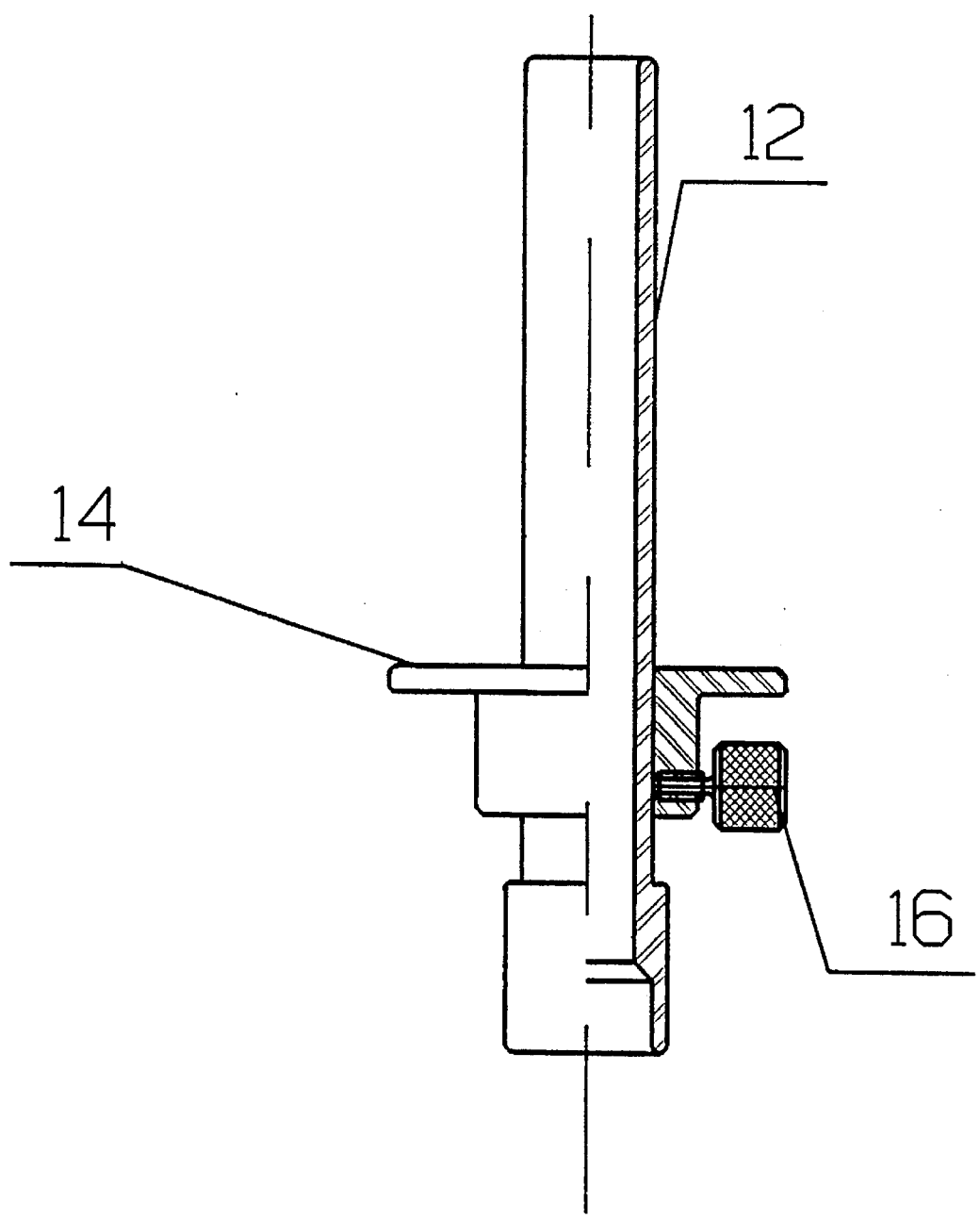
FIG. 1 is a plan view of the outer tube with retention collar.

FIG. 1 is a partially sectioned view of outer tube 12. It is significantly longer than the adult female urethra. Preferably it is a smooth metallic tube of a biocompatible material such as #304 stainless steel. It has a single central lumen sufficiently large to slidably accommodate each of the bladder control device, the insertion rod, and the dilation probe. The walls of outer tube 12 are preferably as thin as possible consistent with the strength requirements of the procedure. The inside and outside dimensions of outer tube 12 are constant except for the very distal end. The distal end of outer tube 12 is flared as shown to accommodate insertion of the proximal end of the device handling tube as described in more detail below.

Retention collar 14 is slidably positioned over the shaft of outer tube 12 as shown. It has a flat distal surface for engagement of the meatus of the patient as shown in detail below. Thumb screw 16 is utilized to removably hold retention collar 14 at a selected longitudinal position along the shaft of outer tube 12.

Figure 2:
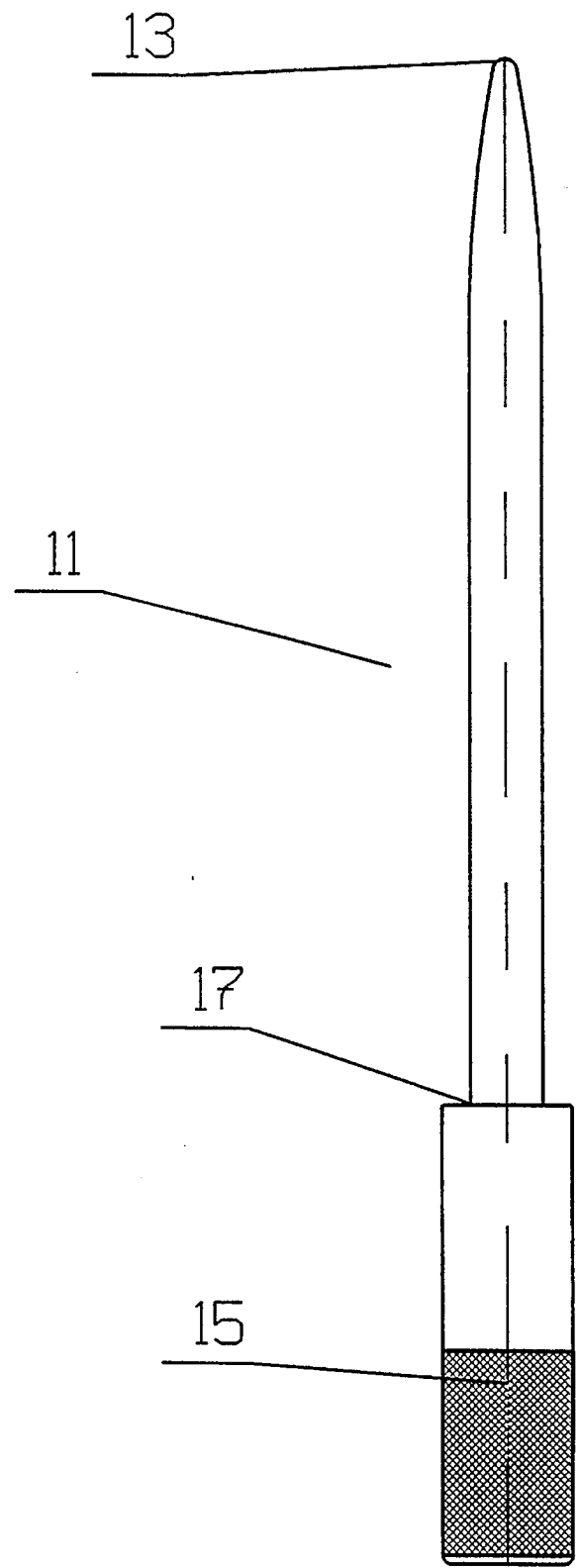
FIG. 2 is a plan view of the dilation probe.

FIG. 2 is a plan view of dilation probe 11, which is preferably a solid rod of a biocompatible material, such as #304 stainless steel. It is conically shaped at proximal end 13 to provide a smooth point. Distal end 13 is thus shaped for atraumatic dilation of the urethra. Except for smooth point 13, the shaft of dilation probe 11 proximal of shoulder 17 has a constant outer diameter sized for convenient slidable insertion within the central lumen of outer tube 12. The length of the shaft from distal point 13 to shoulder 17 is greater that the length of outer tube 12.

The distal end of shoulder 17 is greater than the diameter of the central lumen of outer tube 12 to prevent over insertion. The distal end of dilation probe 11 has a convenient textured handle 15 to enhance the grip during the procedure.

Figure 3:
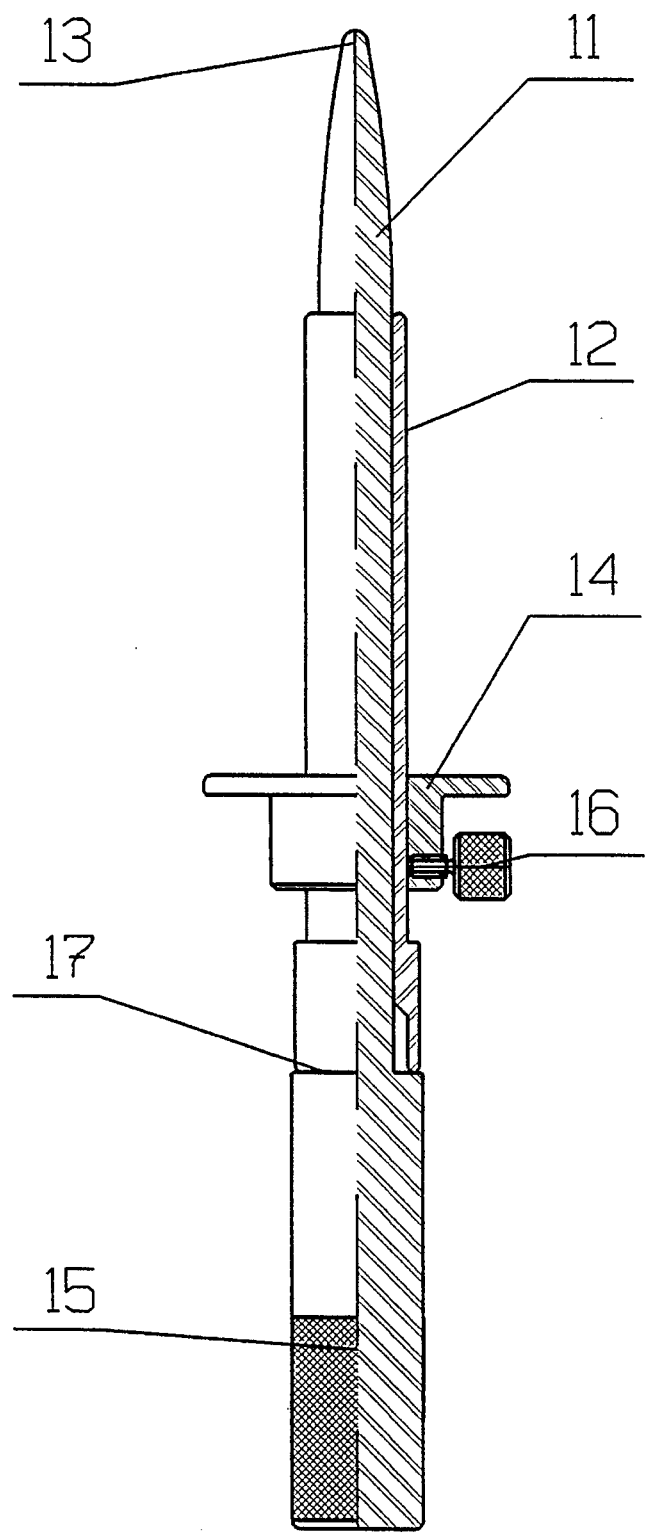
FIG. 3 is a plan view of the dilation probe of FIG. 2 as it appears when placed within the outer tube of FIG. 1.

FIG. 3 is a partially sectioned view of outer tube 12 with dilation probe 11 inserted to the maximum. As can be seen, shoulder 17 acts as a stop against the distal tip of outer tube 12. The remaining elements are as previously discussed.

Figure 4:
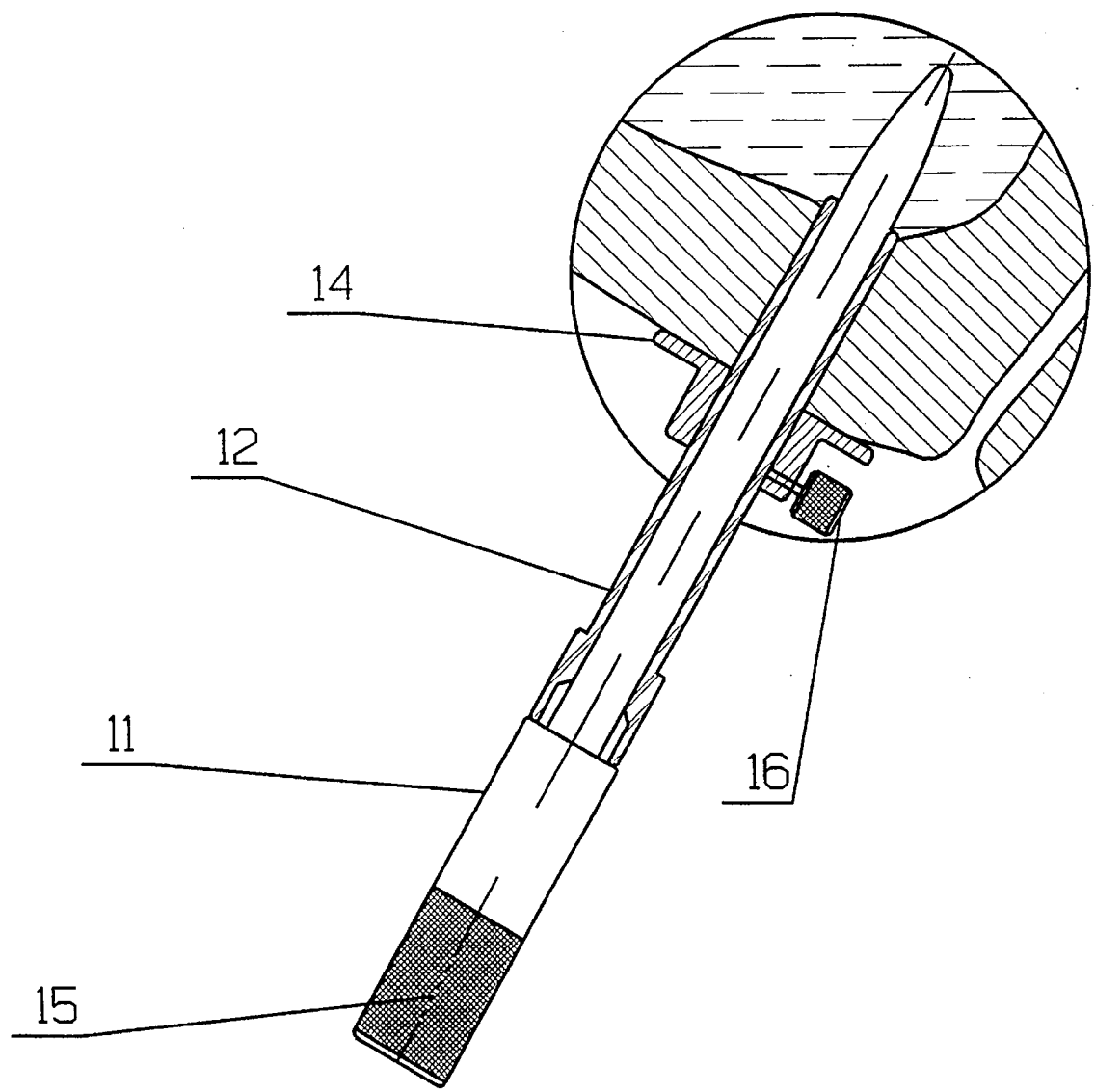
FIG. 4 is a plan view showing the outer tube of FIG. 1 and dilation probe of FIG. 2 assembled together and placed within the urethra.

FIG. 4 is a partially sectioned view of outer tube 12 and dilation probe 11 after insertion into the partially sectioned urethra of a female patient. During the procedure, the assembly of FIG. 3 is inserted into the urethra using localized antiseptic, lubrication, and pain control. Smooth point 13 atraumatically dilates the urethra for entry of outer tube 12. Upon proper insertion, the proximal end of outer tube 12 extends about 1 cm. into the bladder. Note that smooth point of dilation probe 11 extends even further proximally.

After the proper position of outer tube 12 has been established, retention collar 14 is moved proximally along outer tube 12 until it impinges upon the meatus of the patient. Retention collar 14 is held in place by tightening thumb screw 16 against outer tube 12.

Figure 5:
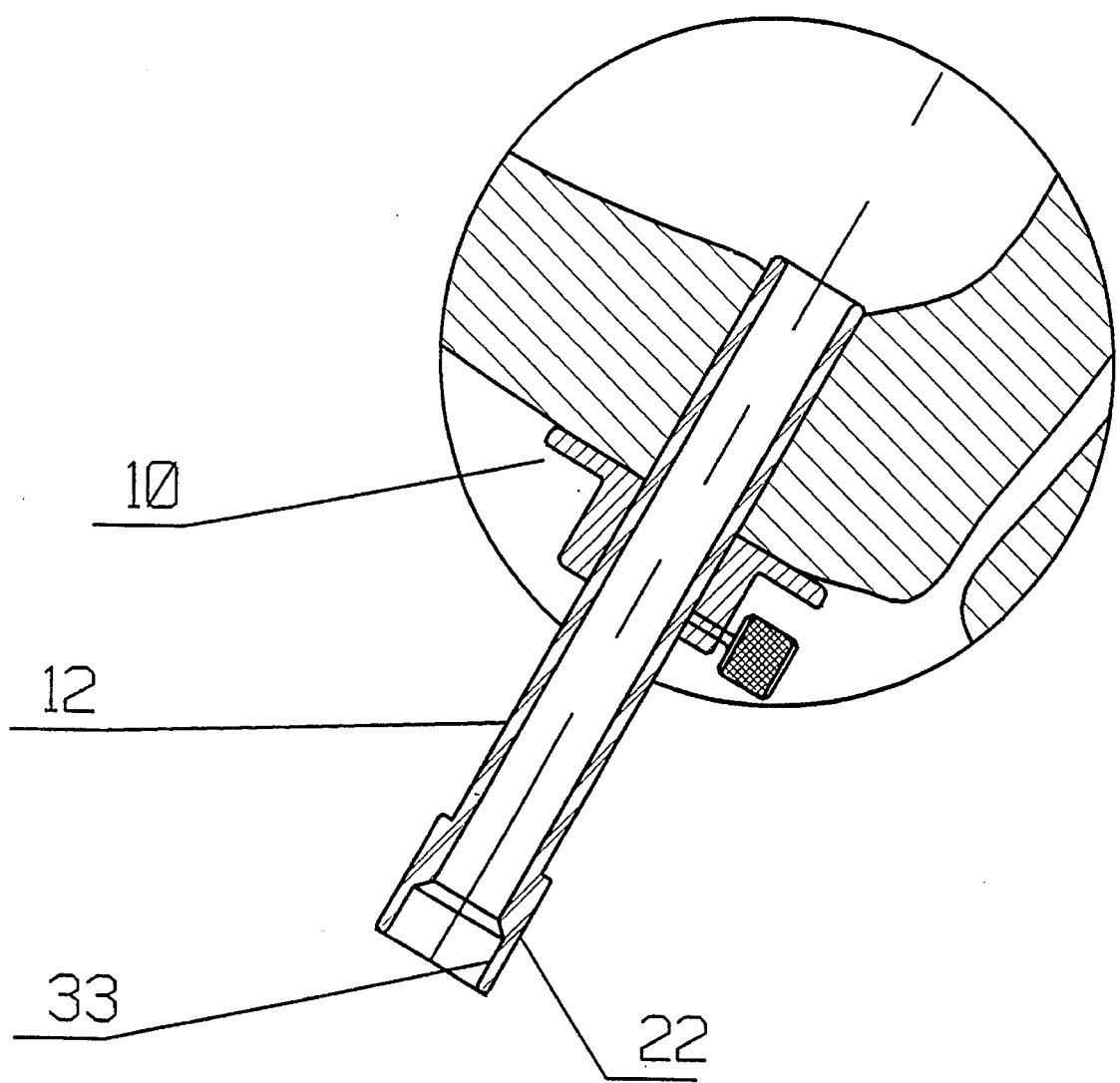
FIG. 5 is a plan view similar to that of FIG. 4 with the dilation probe of FIG. 2 removed from the outer tube of FIG. 1.

FIG. 5 is a sectioned view of the assembly of FIG. 4 with dilation probe 11 completely removed distally. At this place in the procedure, outer tube 12 provides a stable conduit along the entire length of the urethra. The remaining elements are as previously described.

Figure 6:
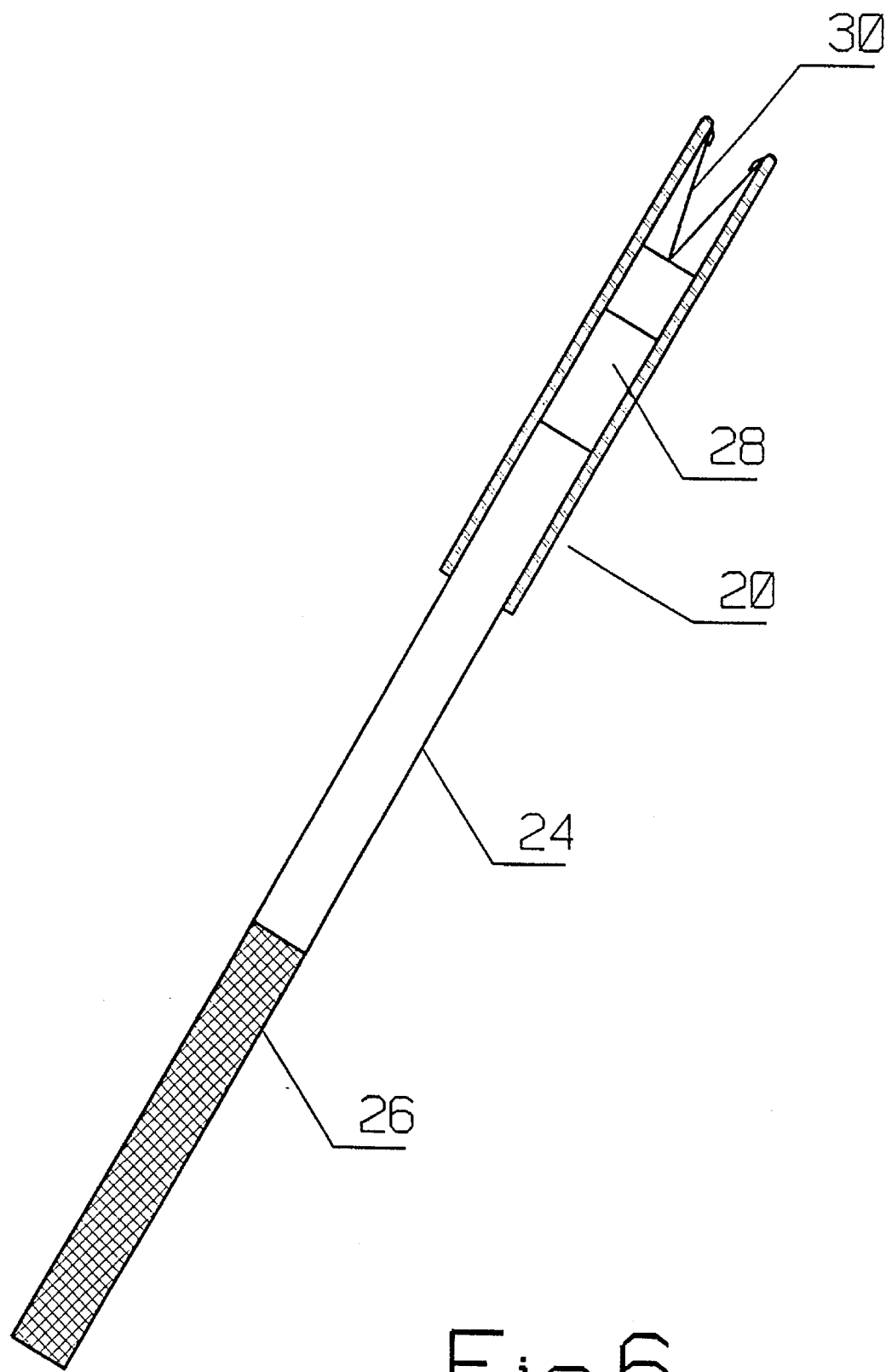
FIG. 6 is a partially sectioned view of the device handler tube containing a bladder control device removably coupled to an insertion rod.

FIG. 6 is a partially sectioned view of bladder control device 28 as loaded into device handler tube 20 and removably attached to insertion rod 24. Device handler tube 20 is preferably a stainless steel tube which is shorter than outer tube 12 but has similar inside and outside dimensions. Bladder control device 28 has proximal retaining springs 30 which are compressed as shown upon being loaded into the proximal end of device handler tube 20.

Insertion rod 24 is preferably a solid stainless steel rod which readily slides within the lumen of device handler tube 20 (and hence outer tube 12 as shown below). The distal end of bladder control device 28 is compatibly tapped to engage the threaded proximal end of insertion rod 24. This creates a readily removable coupling between the distal end of bladder control device 28 and the proximal end of insertion rod 24. Handle 26 of insertion rod 24 is textured to enhance the grip during the procedure.

Figure 7:
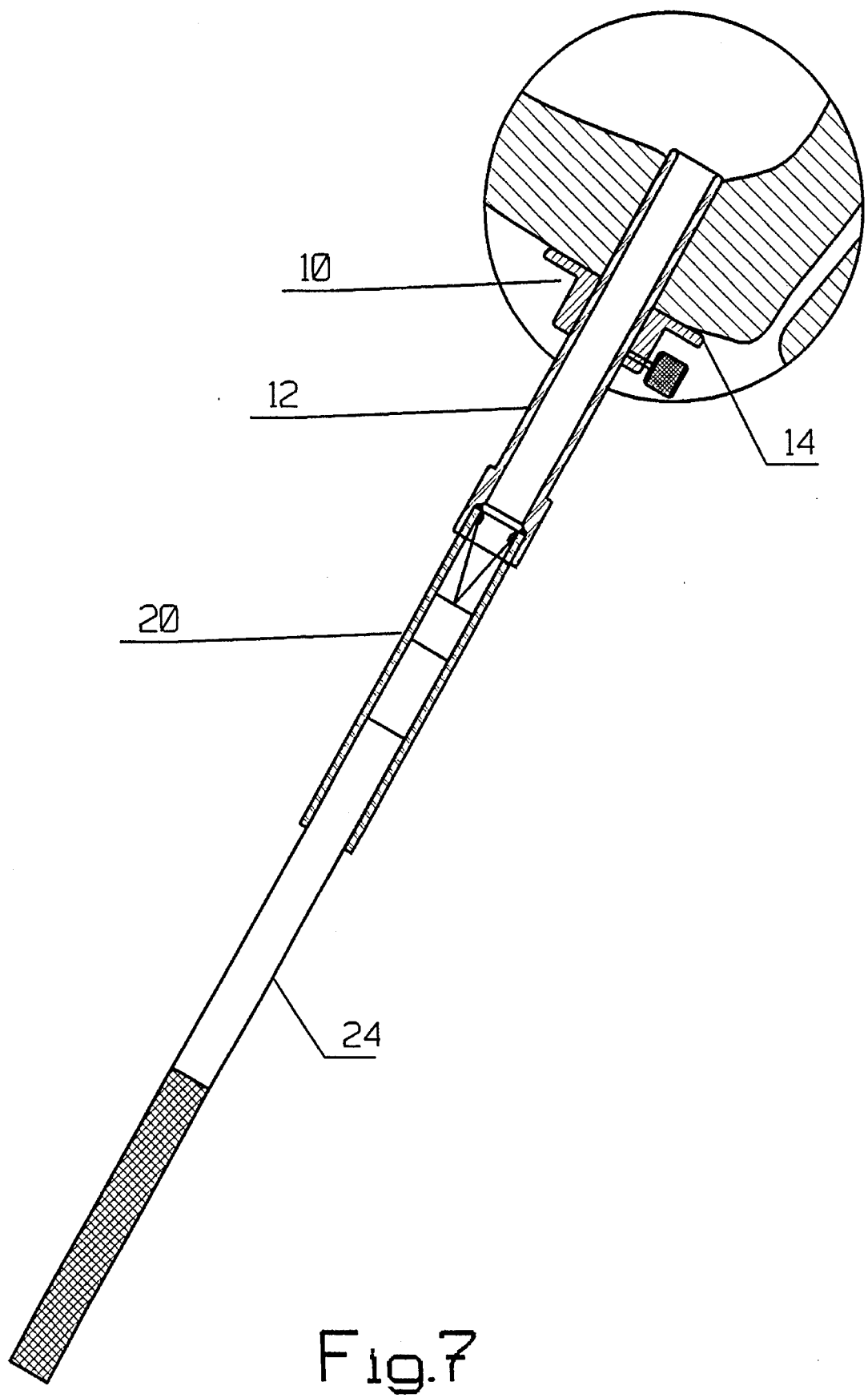
FIG. 7 is a partially sectioned view showing the position for loading of the bladder control device from the device handler tube into the outer tube.

FIG. 7 is a partially sectioned view of the insertion assembly of FIG. 6 engaged in the distal flare of outer tube 12 as positioned in FIG. 5. Note that device handler tube 20 and the main shaft of outer tube 12 have the same radial dimensions which prevents advancement of device handler tube 20 proximally of the distal flare of outer tube 12. From this view it can be seen that bladder control device 28 may be advanced proximally from device handler tube 20 into outer tube 12 while continuing to restrain retention springs 30 using a small force on handle 26° Other elements are as previously explained.

Figure 8:
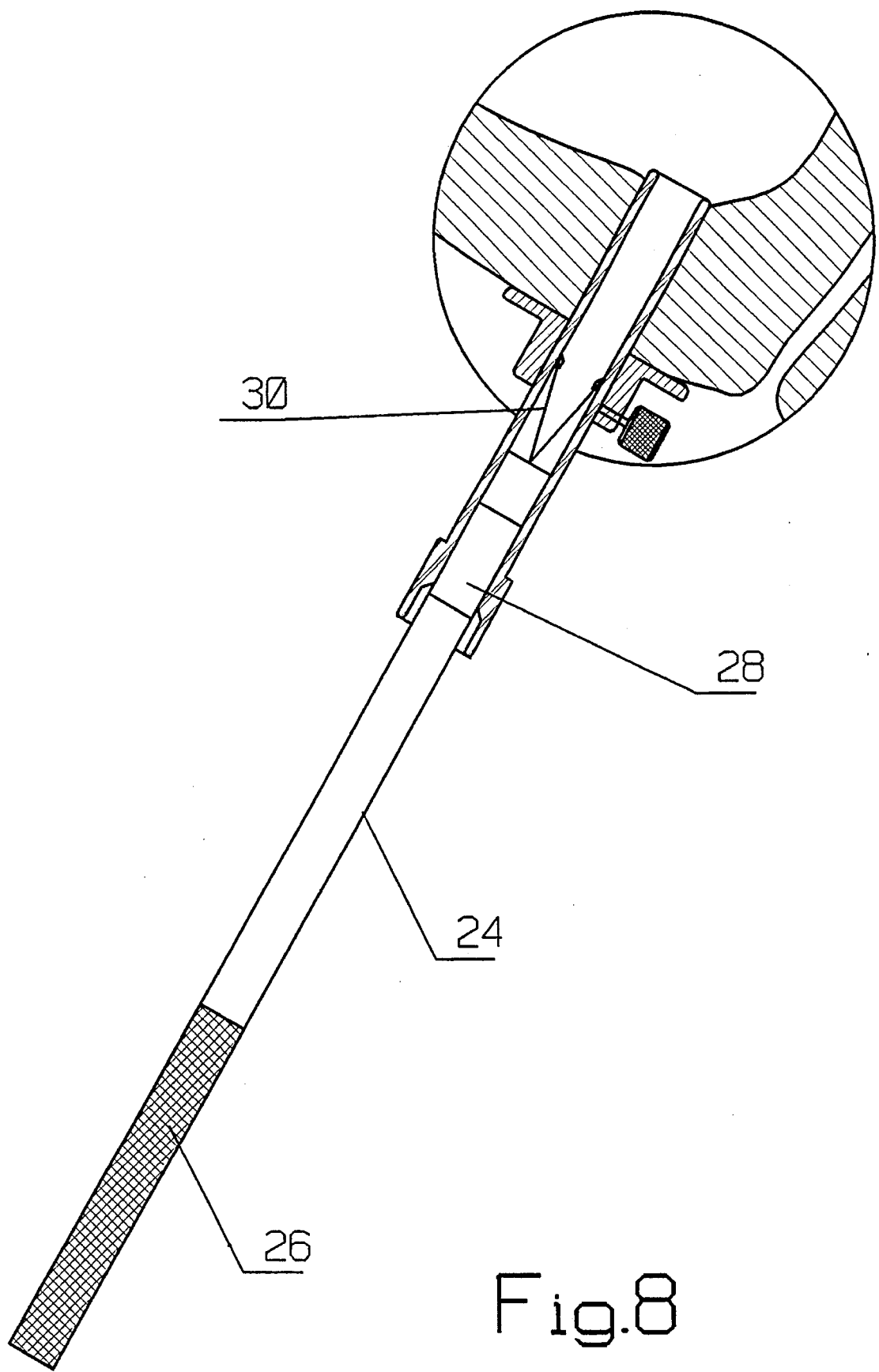
FIG. 8 is a similar view showing the position after completion of the loading with the device handler tube removed.

FIG. 8 is a partially sectioned view of the apparatus of FIG. 7 with device handler tube 20 removed. After bladder control device 28 has been advanced proximally into outer tube 12, device handler tube 20 is removed by sliding over handle 26 distally. The remaining elements are as previously described.

Figure 9:
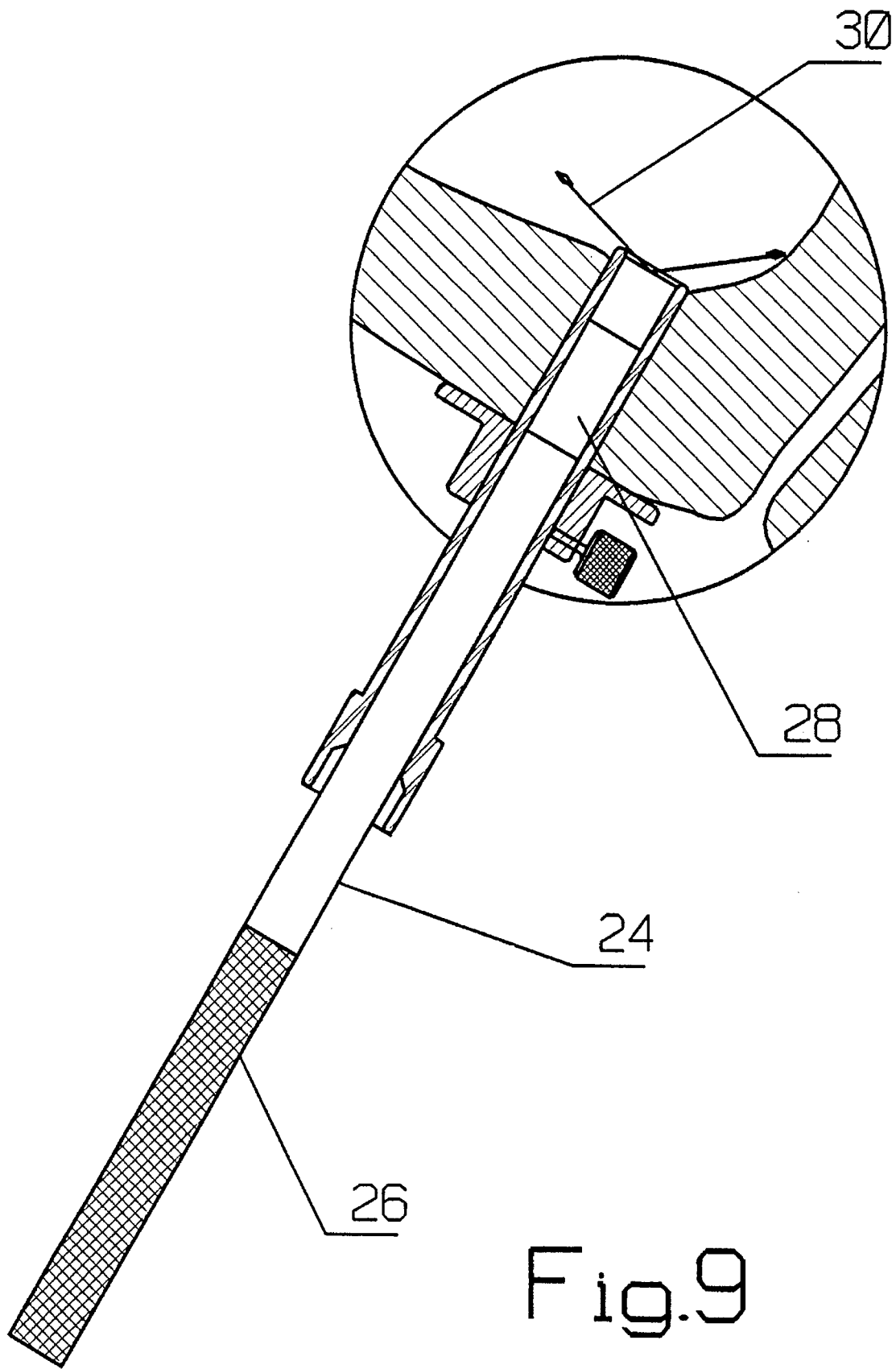
FIG. 9 shows a bladder control device in place within the urethra.

FIG. 9 is a partially sectioned view similar to FIG. 8 wherein bladder control device 28 is advanced proximally through outer tube 12. Retaining springs 30 spread open within the bladder of the patient as shown upon being advanced proximal to the proximal tip of outer tube 12. Other elements are as previously described.

Figure 10:
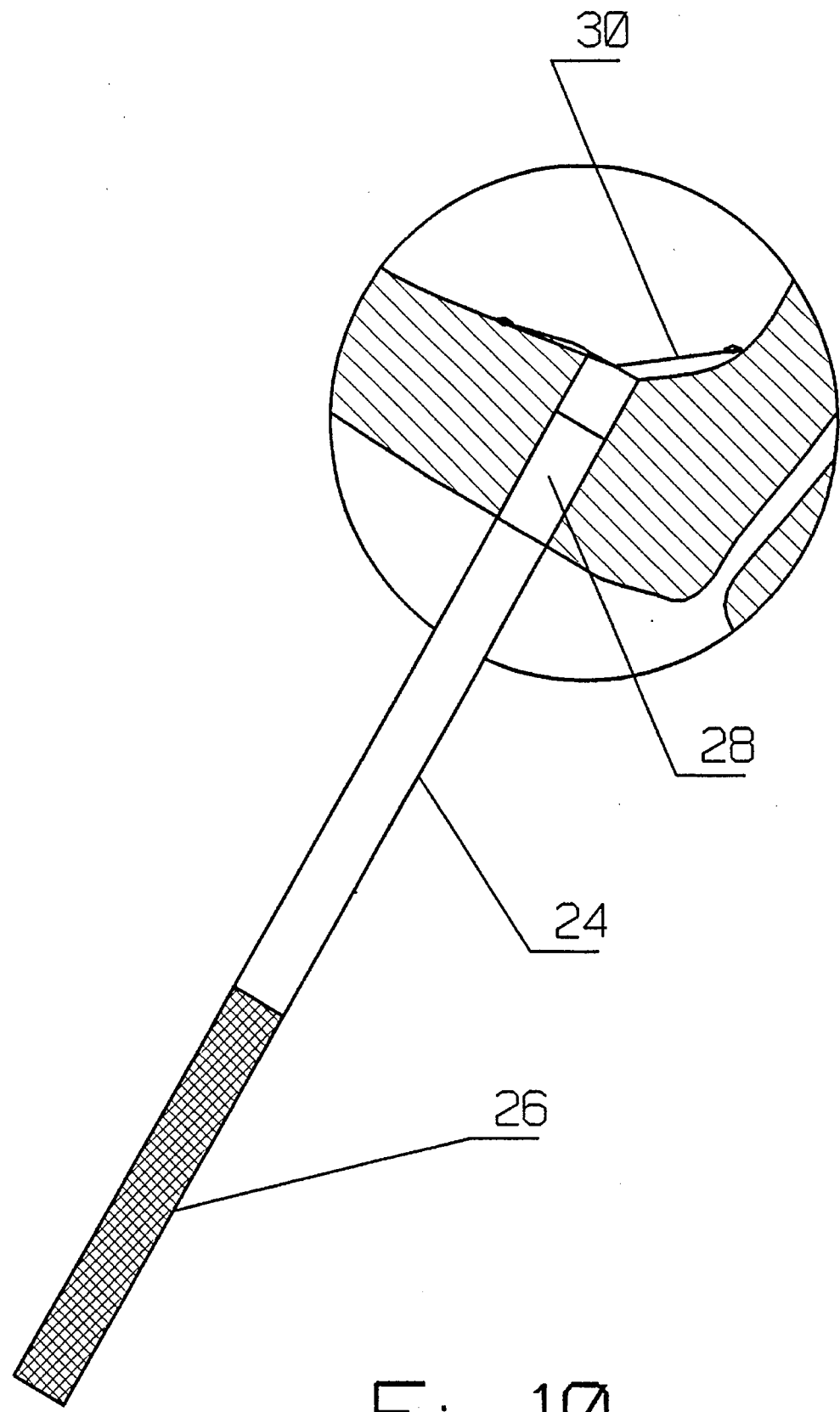
FIG. 10 is a view similar to FIG. 9 after removal of the outer tube and retention collar.

FIG. 10 is a view similar to FIG. 9 following removal of outer tube 12. Outer tube 12 is removed by sliding distally over handle 26. After removal of outer tube 12, insertion rod 24 is pulled distally until retention springs 30 engage the wall of the bladder as shown. Other elements are as previously described.

Figure 11A:
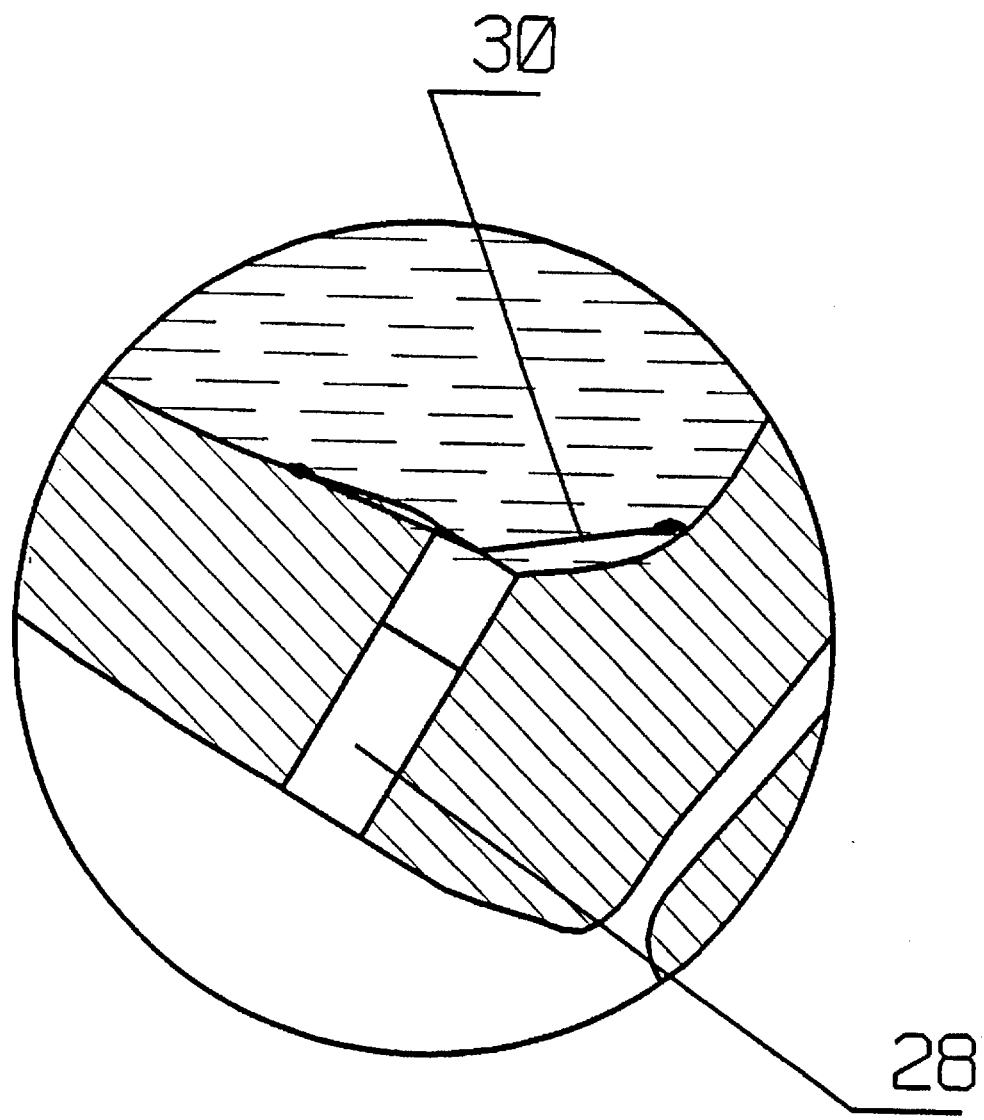
FIG. 11a a is a partially sectioned view showing the properly positioned bladder control device after removal of the insertion rod.

FIG. 11a is a view similar to that of FIG. 10 after removal of insertion rod 24. Bladder control device 28 and insertion rod 24 are decoupled by unscrewing insertion rod 24 via handle 26. At this point bladder control device 28 occupies the entire length of the urethra. To accommodate varying lengths between patients, a bladder control device extension may be required as is explained in the above referenced commonly assigned application which was incorporated herein by reference. Other elements are as previously described.

Figure 11B:
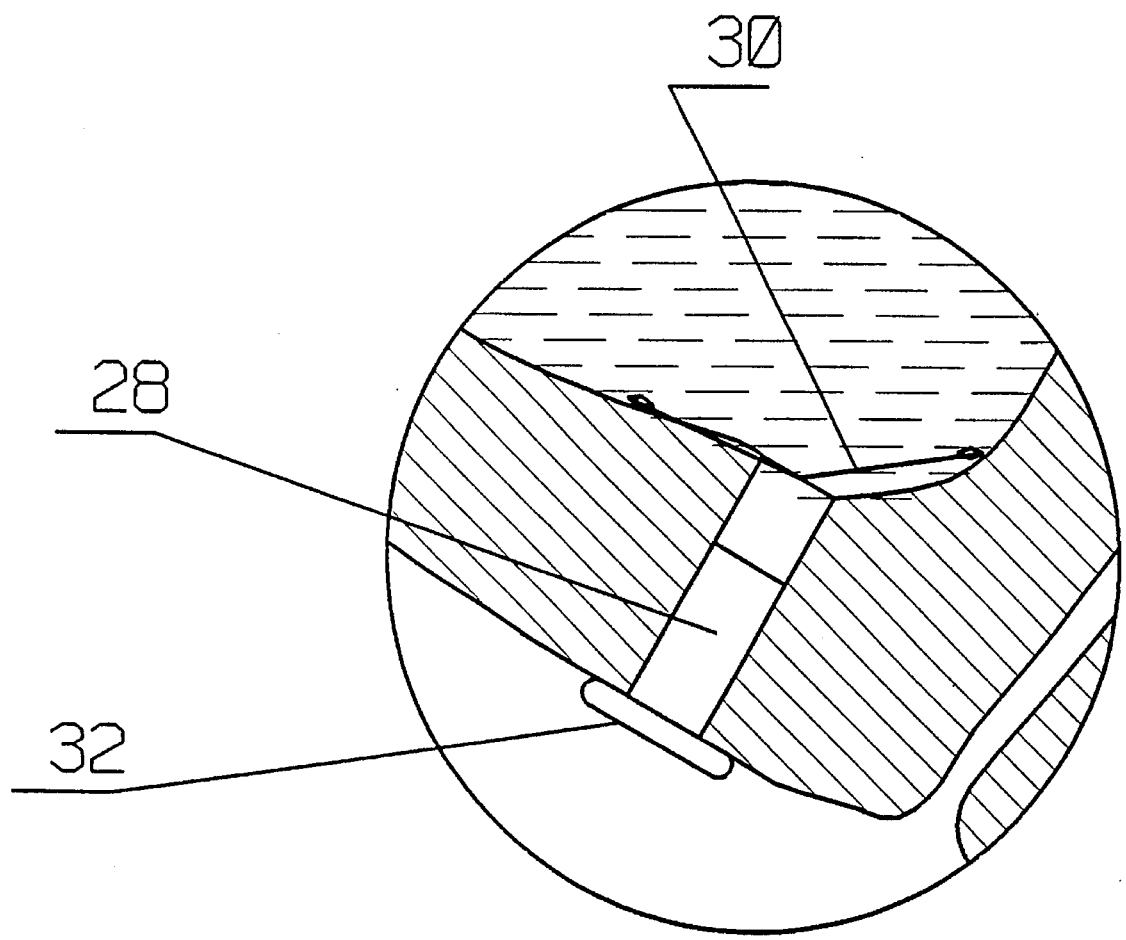
FIG. 11b is a view similar to FIG. 11a after attachment of the distal retaining ring.

FIG. 11b is a view similar to FIG. 11a wherein distal retaining ring 32 is removably attached to the distal end of bladder control device 28. In the preferred mode, distal retaining ring 32 has threads compatible with those tapped into the distal end of bladder control device 28. After insertion rod 28 has been removed, distal retention ring 32 is readily screwed into bladder control device 28 in its place. The resulting assembly is removably secured from distal movement by retaining springs 30 and from proximal movement by distal retention ring 32.

Bladder control device 28 may be readily removed from the urethra using the opposite of the above described procedure.

Having thus described the preferred embodiments of the present invention, those of skill in the art will be readily able to practice yet other embodiments within the teachings found herein and within the scope of the following claims.

What is claimed is:

1. Insertion apparatus for urethral placement of bladder control apparatus having a proximal end and a distal end, the insertion apparatus comprising:
   a. a first tube having a first interior lumen and including distal and proximal ends;
   b. calibration means connected to the exterior of said first tube for setting the depth of insertion of the distal end of said first tube, said calibration means including stop means for contacting the body of a patient adjacent to the urethral entrance;
   c. probe means for slidable mounting within said first lumen, said probe means having a tapered distal end and including further stop means mounted to the exterior thereof for limiting extension of said probe means distal end beyond said first tube distal end;
   d. applicator means for slidable insertion into said first lumen, including means for removably carrying a bladder control apparatus for slidable positioning within said first lumen; and
   e. retention means for mounting on the bladder control apparatus for retaining the apparatus within the urethra after removal of the first tube.

2. The apparatus of claim 1 in which said applicator means includes: a second the defining a second interior lumen of sufficient dimension to slidably receive a bladder control apparatus, said second tube having an exterior dimension sized for slidable movement into at least a portion of said first lumen.

3. The apparatus of claim 2 in which said applicator means further includes: an insertion rod having distal and proximal ends, and having an external dimension sized for slidable movement within said second lumen, said rod distal end including means for removable connection to the distal end of a bladder control apparatus.

4. The apparatus of claim 2 or 3 including: applicator stop means mounted on the exterior of said second tube for limiting the slidable movement of said second tube within said first lumen.

5. The apparatus of claims 2 or 3 in which said retention means includes at least a portion automatically operable when the bladder control apparatus distal end is positioned adjacent said proximal ends of said first and second lumens.

6. The apparatus of claim 4 in which said retention means includes at least a portion automatically operable when the bladder control apparatus proximal end is positioned adjacent said proximal ends of said first and second lumens.

7. The method of placing a medical apparatus within the urethra of a patient comprising the steps of:
   a. providing a first tube having a first lumen;
   b. dilating the uretha with an insertion probe slidably mounted within the first lumen;
   c. sliding the first tube into the dilated urethra;
   d. removing the probe;
   e. providing a second tube having a second lumen, and an insertion rod for slidable movement through the second lumen;
   f. attaching the insertion rod to a medical apparatus;
   g. sliding the medical apparatus into the second lumen with the insertion rod;
   h. sliding the second tube into the first lumen;
   i. removing the first tube and second tubes from the urethra by sliding them over the insertion rod;
   j. disconnecting the rod from the medical apparatus; and
   k. retaining the medical apparatus within the urethra during steps i, j, and k, and thereafter.

8. The method of claim 7 including the step of: limiting the distance the probe extends beyond the urethra.

9. The method of claim 7 including the step of: limiting the depth of insertion of the first tube into the urethra.

10. The method of claim 7 or 8 including the step of: limiting the length of insertion of the second tube into the first lumen.

\* \* \* \* \*